United States Patent [19]

Lindstrom et al.

[11] Patent Number: 4,945,080

[45] Date of Patent: Jul. 31, 1990

[54] DIRITHROMYCIN METABOLITE

[75] Inventors: Terry D. Lindstrom; Gary W. Whitaker, both of Indianapolis, Ind.

[73] Assignee: Eli Lilly and Company, Indianapolis, Ind.

[21] Appl. No.: 53,642

[22] Filed: May 26, 1987

[51] Int. Cl.$^5$ .................. A61K 31/70; C07H 17/08
[52] U.S. Cl. .................. 514/29; 536/7.2; 536/7.4
[58] Field of Search .................. 536/7.1, 7.2, 7.4; 514/29

[56] References Cited

U.S. PATENT DOCUMENTS 3,772,270  11/1973  Gerzon et al. .................. 260/210 E
4,048,306   9/1987  Maier et al. .................. 424/130
4,755,385   7/1988  Etienne et al. .................. 514/29

OTHER PUBLICATIONS

T. Lazarevski et al., "Erythromycin Series v. Quantitative Analysis of Cladinose and Methylcladinoside by Densitometry of Thin-Layer Chromatograms", *J. Chromatography* 132, 309–313 (1977).

M. Chen and W. L. Chiou, "Analysis of Erythromycin in Biological Fluids by High-Performance Liquid Chromatography with Electrochemical Detection", *J. Chromatography* 278, 91–100 (1983).

*Primary Examiner*—Johnnie R. Brown
*Assistant Examiner*—Elli Peselev
*Attorney, Agent, or Firm*—Nancy J. Harrison; Leroy Whitaker

[57] ABSTRACT

Novel macrolide, AS-E 136 metabolite, is obtained from the body fluids of animals receiving AS-E 136 or erythromycylamine. Methods for treating infections caused by pathogenic bacteria, especially Gram-positive bacteria, and pharmaceutical compositions containing the metabolite are provided.

3 Claims, 2 Drawing Sheets

DIRITHROMYCIN METABOLITE

SUMMARY OF THE INVENTION

This invention relates to a novel macrolide compound, designated AS-E 136 metabolite, which has useful antibacterial activity. The compound was discovered in the body fluids, particularly in the plasma and urine, of animals which had been treated with either the novel macrolide antibiotic AS-E 136 or with erythromycylamine.

DETAILED DESCRIPTION OF THE INVENTION

Many beneficial antibiotics are available, but the need for improved antibiotics for use in human medicine continues. Increased potency, expanded spectrum of bacterial inhibition, increased in vivo efficacy and improved pharmaceutical properties (such as greater oral absorption, higher blood or tissue concentrations, longer body half-life and more advantageous rate or route of excretion and rate or pattern of metabolism) are desirable attributes for improved antibiotics.

This invention relates to the discovery that two known antibiotics, AS-E 136 and erythromycylamine, are metabolized in certain mammals to form a compound which is in itself an effective antibiotic. The new antibiotic is designated AS-E 136 metabolite. Like the compounds from which it is formed, AS-E 136 metabolite is also a macrolide antibiotic. It is isomeric with, but differs substantially in structure from erythromycylamine.

AS-E 136 metabolite was first found in the plasma of dogs which had received AS-E 136 orally. The antibiotic AS-E 136 is an oxazine derivative of erythromycylamine. The structure of AS-E 136 is shown in formula 1:

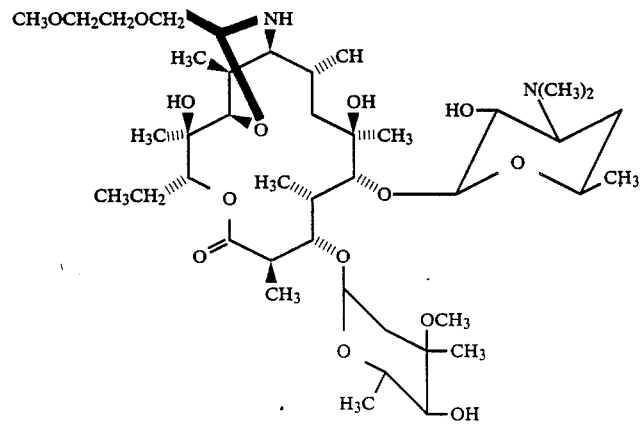

A chemical name for AS-E 136 is 9deoxo-11-deoxy-9,11-[imino[2-(2-methoxyethoxy)ethylidene]oxy](9S)-erythromycin. This compound can be prepared as described by Maier et al. in U.S. Pat. No. 4,048,306, issued Sept. 13, 1977 (See Example 3a).

Later, we discovered that AS-E 136 metabolite is also formed in the urine of dogs following administration of erythromycylamine. The structure of erythromycylamine is shown in formula 2.

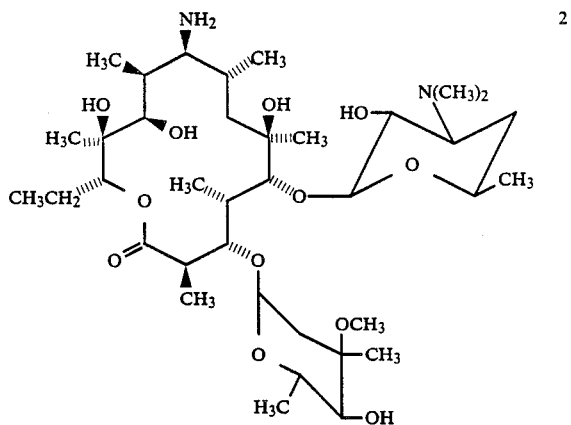

Erythomycylamine can be prepared from erythromycin [see, for example, Massey and Kitchell, U.S. Pat. No. 3,652,537; and Wildsmith, U.S. Pat. Nos. 3,790,559 and 3,780,019].

The compound of this invention, AS-E 136 metabolite, has the following characteristics:

Molecular weight: 734.

Empirical formula: $C_{37}H_{70}N_2O_{12}$ FAB-MS, m/z: 735 (M+H), 577, 158 FD-MS, m/z: 735 (M+H), 159 EI-MS, m/z: 577, 158.

Figure 1:
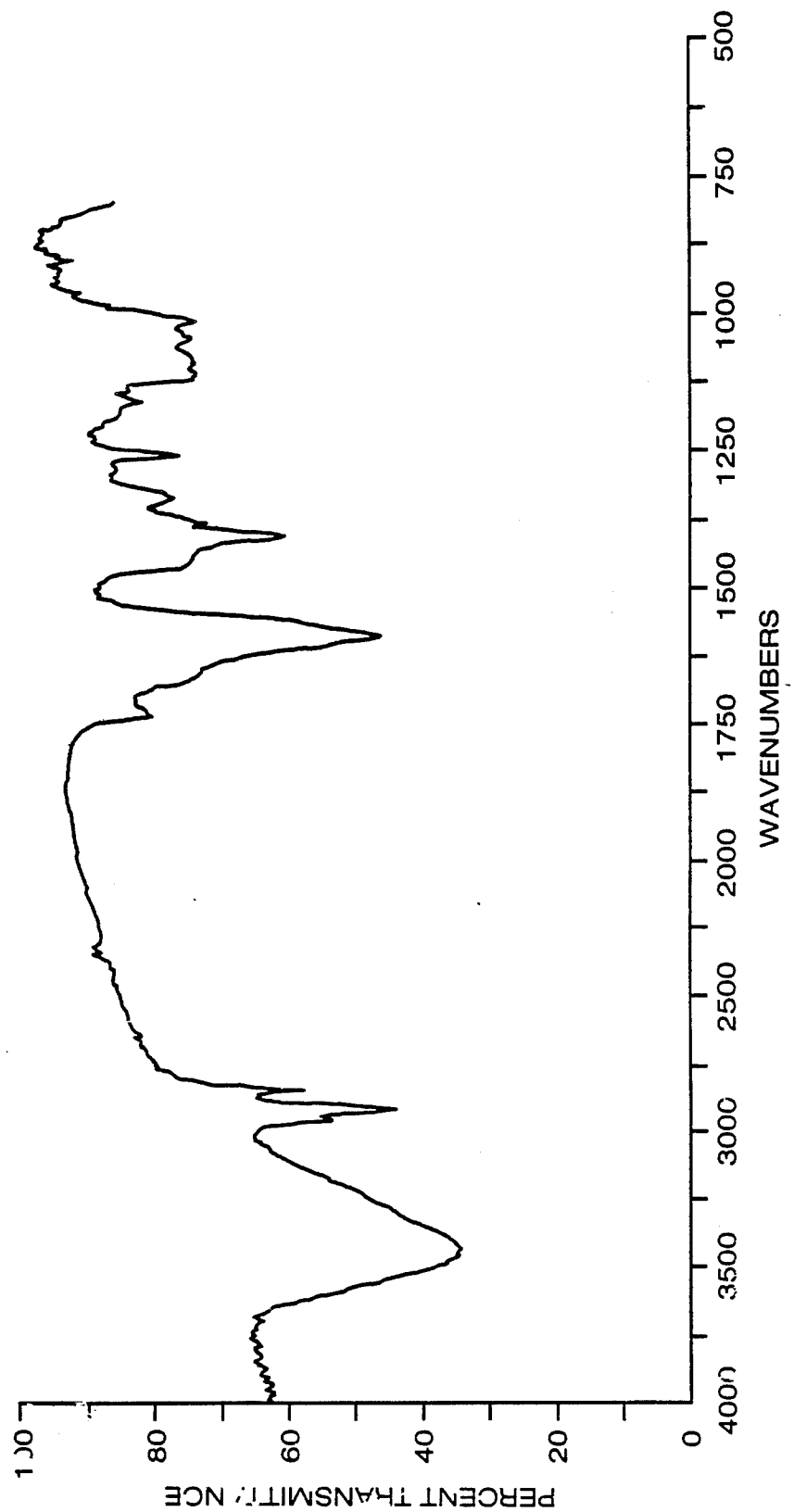
FIG. 1 shows the infrared absorption spectrum of AS-E 136 metabolite in KBr disc.

IR (KBr): 3430 (broad), 2980, 2920, 2853, 1736, 1685, 1656, 1590, 1450, 1408, 1384, 1339, 1260, 1165, 1119, 1107, 1095, 1047 and 1015 cm$^{-1}$ (see FIG. 1)

500 MHz $^1$H NMR (CDCl$_3$) (See FIG. 2):

| Significant Resonances | δ |
| --- | --- |
| methyl triplet | 0.85 |
| methyl doublet | 1.07 |
| " | 1.09 |
| " | 1.14 |
| methyl singlet | 1.21 |
| methyl doublet | 1.21 |
| " | 1.23 |
| " | 1.30 |
| methyl singlet | 1.30 |
| " | 1.43 |
| N(CH$_3$)$_2$ | 2.23 |
| OCH$_3$ | 3.27 |

-continued

| Significant Resonances | δ |
| --- | --- |
| doublet | 2.99 |
| doublet of quartets | 3.04 |
| doublet of doublets | 3.22 |
| doublet | 3.44 |
| doublet of quartets | 4.00 |
| doublet | 4.25 |
| doublet of doublets | 4.34 |
| doublet of doublets | 5.17 |
| doublet | 5.19 |

The metabolite of this invention can form salts. Acid addition salts are particularly useful as antibiotics and are a part of this invention. In another aspect, salts are useful as intermediates, for example, for separating and purifying the metabolite. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention. Pharmaceutically acceptable acid addition salts are those salts useful in the chemotherapy of a warm-blooded animal.

The metabolite of this invention appears to have antibacterial activity that is equal to or greater than that of erythromycylamine. For example, a 10-μg sample of AS-E 136 metabolite in 100 μL of acetonitrile was tested in the following in vitro system:

Two-fold serial dilutions were made from 100 to 0.78 μg/mL. Duplicate levels of each concentration (10 μL) were pipetted into selected wells of a Costar microtiter plate. Samples were assayed using standard techniques by inoculating the wells with 100 μL of medium containing either *Micrococcus luteus* or *Bacillus subtilis*. The plates were incubated overnight at 37° C.

The results observed are summarized below:

| | MIC (μg/mL) | |
| --- | --- | --- |
| Organism | Metabolite | Erythromycylamine |
| B. subtilis | 1.56 | 1.56 |
| M. luteus | ≦0.78 | 1.56 |

Pharmaceutical formulations of AS-E 136 metabolite or a pharmaceutically acceptable salt of AS-E 136 metabolite are also part of this invention. The metabolite, preferably as a pharmaceutically acceptable salt, can be formulated for oral or parenteral administration for treating bacterial infections either therapeutically or prophylactically. For example, a compound of this invention can be admixed with conventional pharmaceutical carriers and excipients and used in the form of tablets, capsules, elixirs, suspensions, syrups, wafers and the like.

The compositions comprising a compound of this invention will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the compound can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained release or enterically coated preparations may also be devised. For pediatric and geriatric applications, suspensions, syrups and chewable tablets are especially suitable.

Alternatively, the unit dosage form can be a solution of the compound or preferably a salt thereof in a suitable diluent in sterile, hermetically sealed ampoules. The concentration of the antibiotic in the unit dosage may vary, e.g. from about 1 percent to about 50 percent, depending on the compound used and its solubility and the dose desired by the physician.

In a further aspect, this invention provides a method for treating infectious diseases, especially those caused by Gram-positive bacteria, in animals. The term "treating" is used to denote both the prevention of infectious diseases and the control of such diseases after the host animal has become infected. The method comprises administering to the animal an effective dose of a compound of this invention. An effective dose is generally between about 0.1 and about 100 mg/kg of the compound or its pharmaceutically acceptable salt. A preferred dose is from about 1 to about 30 mg/kg of compound. A typical daily dose for an adult human is from about 100 mg to about 1.0 g.

In practicing this method, the antibiotic compound can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic orally, using tablets, capsules, suspensions, syrups and the like. The antibiotic may also be administered by other methods, e.g. as a suppository or parenterally via IV infusion.

The following examples are provided to illustrate the operation of this invention.

EXAMPLE 1

Isolation of AS-E 136 Metabolite From Dog Plasma

A. Administration of AS-E 136

AS-E 136 is prepared for administration to young, adult beagle dogs in enteric coated capsules as follows:

| Lot Numbers of Enteric Coated Capsules | Starch Flowable | (Theoretical Concentration) | | |
|---|---|---|---|---|
| | | Starch Powder | AS-E 136 | MgCO$_3$ |
| 1* | 190 | — | — | — |
| 2 | — | 200 | 10 | — |
| 3 | — | 370 | 100 | — |
| 4 | — | 90 | 250 | — |
| 5 | — | 190 | 10 | 10 |
| 6 | — | 120 | 100 | 100 |
| 7 | — | 190 | — | 10 |
| 8 | — | 300 | — | 100 |

*Also contains 40 mg starch flowable with 5% silicone.

The administered doses are prepared as follows:

| Treatment Group | Dose (mg/kg) | | Preparation$^a$ |
|---|---|---|---|
| | AS-E 136 | MgCO$_3$ | |
| 0 | 0 | 0 | Place 6 enteric coated placebo starch capsules (lot 1) in gelatin capsules |
| 1 | 0 | 30 | Place enteric coated capsules of MgCO$_3$ (lots 7 and 8) in gelatin capsules |
| 2 | 30 | 30 | Place enteric coated capsules of AS-E 136/MgCO$_3$ (lots 5 and 6) in gelatin capsules |
| 3 | 30 | 0 | Place enteric coated capsules of AS-E 136 (lots 2, 3 and 4) in gelatin capsules |
| 4 | 70 | 0 | Place enteric coated capsules of AS-E 136 (lots 2, 3 and 4) in gelatin capsules |
| 5 | 150 | 0 | Place enteric coated capsules of AS-E 136 (lots 2, 3 and 4) in gelatin capsules |

$^a$The administered dose is an approximation of the calculated doses, using the most appropriate combination of 10, 100, and 250 mg AS-E 136, 10 and 100 mg AS-E 136/MgCO$_3$, and 10 and 100 mg MgCO$_3$ enteric coated capsules.

The dogs are given a standard diet and observed daily. The animals are treated as follows:

| Treatment Group | Dose (mg/kg) | | Number Animals | |
|---|---|---|---|---|
| | AS-E 136 | MgCO$_3$ | Male | Female |
| 0 | 0 | 0 | 4 | 4 |
| 1 | 0 | 30 | 4 | 4 |
| 2 | 30 | 30 | 4 | 4 |
| 3 | 30 | 0 | 4 | 4 |
| 4 | 70 | 0 | 4 | 4 |

-continued

| Treatment Group | Dose (mg/kg) | | Number Animals | |
|---|---|---|---|---|
| | AS-E 136 | MgCO$_3$ | Male | Female |
| 5 | 150 | 0 | 4 | 4 |

Plasma is removed from the dogs at 30 days and at 90 days at 0, 15 and 30 minutes, 1, 2, 4, 6, 8 and 24 hours after the dose.

B. Plasma Collection and Extraction

Whole blood is collected in sodium heparinized tubes and kept on ice until centrifuged. Blood is spun at approximately 2000 rpm for 10 min, and 0.5-mL of plasma is added to 1.0 mL of pH 10 buffer and stored at $-70°$ C. until analyzed. The 1.5-mL samples are added to 250 ng of internal standard (25 $\mu$g/mL stock in MeOH) in a 15-mL glass centrifuge tube, and 5 mL of dichloromethane is added and mixed for approximately 10 sec.

The sample is centrifuged for 5 min at approximately 2000 rpm. The organic phase (4 mL) is removed and placed in a 15-mL glass centrifuge tube.

The plasma sample is extracted a second time with dichloromethane (5 mL). Organic phase (4 mL) is removed, combined with the first extract and evaporated to dryness under nitrogen at 30°–50° C.

Samples are dissolved in acetonitrile (80 $\mu$L), placed in limited-volume Wisp autoinjector vials and capped. Aliquots (40–60 $\mu$L) are injected onto the HPLC column.

C. HPLC System

Solvent Delivery: Waters Model 6000 pump
Auto Injector: Waters Model 710B Wisp
Column Sepralyte (100 angstrom) di-phenyl 5 $\mu$, 250-x 4.6-$\mu$ i.d. (Part #545809 Analytichem International), maintained at 40° C. using a BAS column block heater controlled by an LC-22 heater control (Bioanalytical Systems, Inc.)
Detector: ESA Coulochem Model 5100A operated in screen mode, equipped with a model 5020 guard cell at a potential of 1.0 volt. A model 5011 analytical cell with the first electrode (coulometric) set in the screen mode at a potential of 0.7 volt and the second electrode (amperometric) set for detection at a potential of 0.9 volt is used. With a sensitivity setting of 400–600 nV the 1.0 volt output is on-line to an HP1000 series 2117F computer for peak integration and to a Fisher Recordall Series 5000 strip chart recorder.
Mobile Phase: 60% CH$_3$CN:10% MeOH:30% H$_2$O containing NH$_4$OAc (3.85 g/L) and NaClO$_4$ (1.45 g/L) to give a final concentration of 40 mM NH$_4$OAc and 10 mM NaClO$_4$. The aqueous phase is adjusted to pH 7.5 with 0.1N NaOH prior to mixing with the organic phase. The aqueous phase is filtered through a 0.22-$\mu$ GS type Millipore filter, and the organic phase is filtered through a 0.5-$\mu$ FH type filter prior to mixing and degassing. The mobile phase is prepared and recirculated for 24 hr prior to analysis. The solvent is recirculated.
Flow rate: 1.0 mL/min
Retention Times: 9-Dihydroerythromycylamine: approximately 8.0 min. AS-E 136: approximately 10 min, k'=1.25. Erythromycylamine: approximately 18 min, k'=2.25.

The HPLC system is very sensitive to changes in the mobile phase; therefore, standards must be chromatographed and computer parameters assessed before the start of each group analysis.

Calculations

Ratio of peak height of unknowns to peak height of internal standard are compared to known concentrations of standards using a linear least squares regression.

The assay has been validated for both AS-E 136 and erythromycylamine. A high and low standard curve was prepared for erythromycylamine and a low standard curve was prepared for AS-E 136. The range and relative standard deviation of the standard curves as well as the accuracy and precision of the method is shown below.

| Compound | Run # | Concentration Range | RSD % | Corr. Coef. |
|---|---|---|---|---|
| AS-E 136 | 1 | 50–500 ng/0.5 mL | 2.1 | 0.999 |
| erythromycylamine | 1 | 75–500 ng/0.5 mL | 4.8 | 0.998 |
| erythromycylamine | 2 | 500–6000 ng/0.5 mL | 2.2 | 0.999 |

| Compound | Conc. (ng/0.5 mL) | Accuracy (ng/0.5 mL) | Precision (% RSD) |
|---|---|---|---|
| AS-E 136 | 50 | 51 | 11.4 |
| " | 200 | 202 | 3.3 |
| " | 350 | 349 | 2.1 |
| erythromycylamine | 50 | 56 | 12.4 |
| " | 250 | 246 | 3.5 |
| " | 400 | 402 | 2.6 |

D. Observing the Metabolite

Plasma samples from a toxicology study of AS-E 136 in dogs, carried out as described in Sections A and B, were assayed by HPLC using electrochemical detection and an Alltech diphenyl analytical column as described in Section C. During analysis of plasma samples from dogs which had received AS-E 136 for 30 and 90 days, we observed a metabolite which was not present in the control dosage group samples. The k' values of AS-E 136 and erythromycylamine (a known metabolite of AS-E 136) were 1.39 and 2.43, respectively. The new metabolite had a k' value of 0.67.

E. Isolating the Metabolite

AS-E 136 metabolite was isolated from dog plasma using the following procedure:

Plasma samples from dogs receiving AS-E 136 for 90 days (8 dogs, 0-24-hr samples) were combined, giving a total plasma volume of approximately 450 mL. The plasma was adjusted to pH 10 with 1N NaOH and extracted twice with 1 L of dichloromethane. The dichloromethane extracts were combined and evaporated to dryness under vacuum. The residue obtained was dissolved in 2.0 mL of acetonitrile:water (1:1) for subsequent injection onto HPLC system 1:

HPLC System 1

Column: Alltech Di-phenyl, 250×4.6 mm, 5 μ particle size
Solvent: acetonitrile:methanol:water (6:1:3) containing 40 mM ammonium acetate and 10 mM sodium perchlorate
Flow rate: 1.0 mL/min.

Three sequential injections of the plasma extract were made. Material eluting at the retention time of the metabolite was collected. The eluate was reduced in volume to that of the aqueous component under vacuum and adjusted to pH 9.5 with 1M sodium carbonate buffer (pH 9.5). The solution was extracted twice with dichloromethane (2 volumes), and the dichloromethane extracts were evaporated to dryness under vacuum.

The residue was redissolved in 1.0 mL of acetonitrile:water (1:1) for subsequent injection onto HPLC system 2:

HPLC System 2

Column: Same as System 1
Solvent: acetonitrile:methanol:water (7:1:2)
Flow rate: Same as System 1

Three injections of the extract were made over a 30-minute time span. The mobile phase was then enriched with 40 mM ammonium acetate, and the column eluate was collected for 30 minutes. The eluate was reduced in volume to that of the aqueous component under vacuum and adjusted to pH 9.5 with 1M sodium carbonate buffer (pH 9.5) The solution was extracted twice with dichloromethane (2 volumes), and the dichloromethane extracts were evaporated to dryness under vacuum. The residue was dissolved in 1.0 mL of acetonitrile:water (1:1) and applied to HPLC System 1. The eluate collected at the retention time of the metabolite was reduced in volume to that of the aqueous component under vacuum and adjusted to pH 9.5 with 1M sodium carbonate buffer (pH 9.5). The solution was extracted twice with dichloromethane (2 volumes), and the pooled dichloromethane extracts were evaporated to dryness under vacuum to give AS-E 136 metabolite.

EXAMPLE 2

Isolation of AS-E-136 Metabolite from Dog Urine

AS-E 136 and $^{14}C$-labeled AS-E 136 were mixed with an equal weight of Flowable Powder Starch, and the mixture was placed in size 0 gelatin capsules coated with an enteric coating. Dogs were housed in metabolism cages and fasted overnight prior to dosing. Drug was administered orally at 10 mg/kg to three female hound dogs. Food was offered 6 hr post-dosing. Urine was collected for 24 hr.

Urine samples were extracted at pH 10 with dichloromethane, and extracts were analyzed by HPLC using System 1, supra, and an electrochemical detector for metabolite observation. In addition, 30-second fractions of column eluate were collected and counted for radioactivity. The HPLC radioactivity profile showed a radioactive peak at the retention time observed for AS-E 136 metabolite by electrochemical detection in dog plasma samples.

Urine collected from one of the dogs was adjusted to pH 10 with 5 N NaOH and then was extracted with dichloromethane. The extract was evaporated to dryness under vacuum, and the residue was dissolved in 500 μL of methanol for injection onto an HPLC system identical to System 1 except that the solvent did not contain sodium perchlorate. After the extract was injected, 30-second fractions of column eluate were collected and counted for radioactivity.

Fractions which contained radioactivity at the retention time of AS-E 136 metabolite (7-12) were combined and reduced in volume under vacuum to the volume of the aqueous component and adjusted to pH 10 with pH 10 Fisher SO-B-116 buffer.

The solution was extracted with dichloromethane, and the organic fraction was evaporated to dryness. The residue was dissolved in acetonitrile:methanol:water (7:1:2) and subjected to HPLC, using System 2.

The mobile phase was enriched with 40 mM ammonium acetate 30 minutes after injection, and the column eluate was collected for another 30 minutes. The eluate collected at the AS-E 136 metabolite's retention time was reduced in volume under vacuum to that of the aqueous component, adjusted to pH 10 and extracted with dichloromethane (2 volumes). The organic phase was evaporated to dryness.

The residue was dissolved in acetonitrile:methanol:water (6:1:3) containing 40 mM ammonium acetate and subjected to HPLC, using System 1 and collecting 30-second fractions. Fractions corresponding to the retention time of the metabolite (7-12) were pooled and reduced in volume to that of the aqueous component under vacuum and adjusted to pH 10. This solution was extracted twice with dichloromethane (2 volumes), and the organic phase was evaporated to dryness under vacuum to give AS-E 136 metabolite, as identified by mass spectral analysis.

Figure 2:
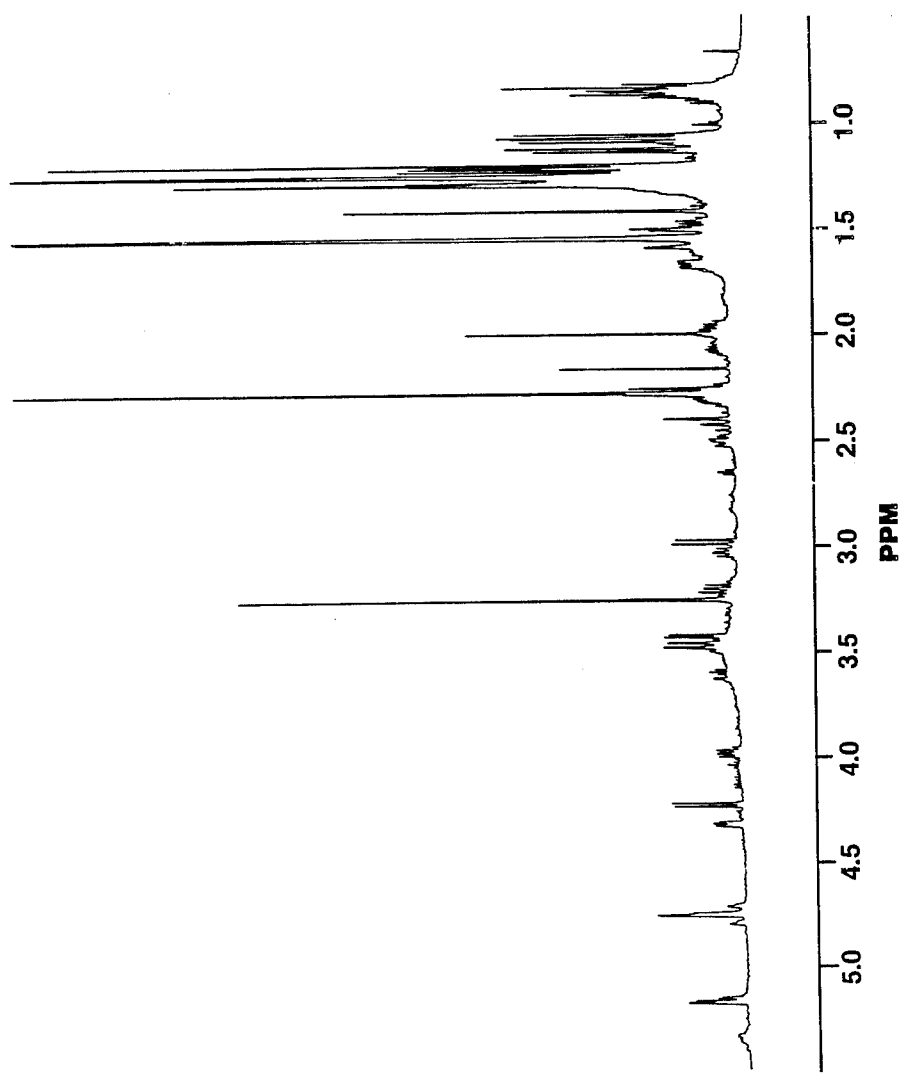
FIG. 2 shows the 500 MHz proton nuclear magnetic resonance spectrum of AS-E 136 metabolite in CDCl$_3$.

We claim:

1. Dirithromycin metabolite, which has these characteristics:
   Molecular weight: 734
   Empirical formula: $C_{37}H_{70}O_{12}N_2$
   FAB-MS, m/z: 735 (M+H), 577, 158
   FD-MS, m/z: 735 (M+H), 159
   EI-MS, m/z: 577, 158
   IR (KBr): FIG. 1
   500 MHz $^1$H NHR(CDCl$_3$): FIG. 2 or a pharmaceutically acceptable acid addition salt thereof, in substantially pure form.

2. A composition useful for the treatment of susceptible bacterial infections comprising an effective antibacterial amount of a compound of claim 1 together with a suitable vehicle.

3. A method for treating infections caused by susceptible bacteria which comprises administering an effective amount of a composition of claim 2 to an animal.

* * * * *

UNITED STATES PATENT AND TRADEMARK OFFICE
CERTIFICATE OF CORRECTION

U.S. PATENT NO. : 4,945,080

DATED : July 31, 1990

INVENTOR(S) : Terry D. Lindstrom et al.

It is certified that an error appears in the above-identified patent and that said Letters Patent is hereby corrected as shown below:

Column 10, line 12, "500 MHz $^1$H NHR(CDCl$_3$): FIG. 2" should read --500 MHz $^1$H NMR(CDCl$_3$): FIG. 2--

Signed and Sealed this

Second Day of November, 1993

*Attest:*

BRUCE LEHMAN

*Attesting Officer*      Commissioner of Patents and Trademarks